United States Patent [19]
Haga et al.

[11] Patent Number: 4,677,110
[45] Date of Patent: Jun. 30, 1987

[54] N-BENZOYL-N'-PYRIMIDINYLOXYPHE-NYL UREA COMPOUNDS, AND ANTITUMOROUS COMPOSITIONS CONTAINING THEM

[75] Inventors: Takahiro Haga, Kusatsu; Nobutoshi Yamada; Hideo Sugi, both of Moriyama; Toru Koyanagi, Kyoto; Hiroshi Okada, Kusatsu, all of Japan

[73] Assignee: Ishihara Sangyo Kaisha Ltd., Osaka, Japan

[21] Appl. No.: 741,134

[22] Filed: Jun. 4, 1985

[30] Foreign Application Priority Data

Jun. 15, 1984 [JP] Japan .................. 59-123399
Apr. 2, 1985 [JP] Japan .................. 60-69426

[51] Int. Cl.$^4$ .................. C07D 239/30; C07D 239/34; A61K 31/505
[52] U.S. Cl. .................. 514/274; 544/316
[58] Field of Search .................. 544/316; 514/269, 274

[56] References Cited
U.S. PATENT DOCUMENTS

B 435,617 3/1976 Johnston .................. 260/256.4
4,321,388 3/1982 Nishiyama et al. .................. 546/291

FOREIGN PATENT DOCUMENTS 57-109721 7/1982 Japan .

OTHER PUBLICATIONS

Derwent Japanese Patent Report, No. 202 (C-129), [1080], 13th Oct. 1982; Abstract of JP 57-109721(A).
Derwent Japanese Patent Report, vol. 5, No. 62 (C-52)[734], 25th Apr. 1981; Abstract of JP 56-15272(A).

Primary Examiner—John M. Ford
Attorney, Agent, or Firm—Oblon, Fisher, Spivak, McClelland & Maier

[57] ABSTRACT

N-benzoyl-N'-pyrimidinyloxyphenyl urea compounds having the formula:

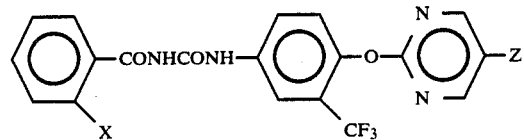

wherein X represents a hydrogen atom, a halogen atom, a nitro group or a trifluoromethyl group and Z represents a hydrogen atom or a halogen atom, are useful as active ingredients of antitumorous compositions.

10 Claims, No Drawings

N-BENZOYL-N'-PYRIMIDINYLOXYPHENYL UREA COMPOUNDS, AND ANTITUMOROUS COMPOSITIONS CONTAINING THEM

BACKGROUND OF THE INVENTION

1. Field of the Invention

The present invention relates to novel N-benzoyl-N'-pyrimidinyloxyphenyl urea compounds, antitumorous compositions containing them as active ingredients, a method for therapy of cancer by using these compounds, and a process for producing these compounds.

2. Discussion of the Background

N-benzoyl-N'-pyridinyloxyphenyl urea compounds are disclosed in U.S. Pat. No. 4,321,388. It is disclosed that these compounds are useful as agricultural chemicals and pharmaceuticals (antitumour drugs). Further, in Japanese Unexamined Patent Publication No. 109721/1982, it is disclosed that N-benzoyl-N'-pyridinyl(pyrimidinyl)oxyphenyl urea compounds are useful as antitumour drugs.

However, it is not known that novel N-benzoyl-N'-pyrimidinyloxyphenyl urea compounds wherein the benzoyl group has a hydrogen atom, a halogen atom, a nitro group or a trifluoromethyl group at the 2-position, the phenyl group has a trifluoromethyl group at the 3-position, and the pyrimidinyl group has a hydrogen atom or a halogen atom at the 5-position, have high antitumour activities.

SUMMARY OF THE PRESENT INVENTION

The present inventors have conducted extensive researches on the changes of the substituents for N-benzoyl-N'-pyrimidinyloxyphenyl urea compounds, and have finally found that novel N-benzoyl-N'-pyrimidinyloxyphenyl urea compounds wherein the benzoyl group has a hydrogen atom, a halogen atom, a nitro group or a trifluoromethyl group at the 2-position, the phenyl group has a trifluoromethyl group at the 3-position, and the pyrimidinyl group has a hydrogen atom or a halogen atom at the 5-position, have high antitumour activities.

DETAILED DESCRIPTION OF THE PREFERRED EMBODIMENTS

The compounds of this type are generally hardly soluble in both water and organic solvents, and accordingly poorly absorbable by the gut. Therefore, depending upon the manner of administration, they sometimes hardly exhibit antitumour activities, and there is a limitation for the intraperitoneal administration of such drugs for curing purposes. Whereas, it has been found that the compounds of the present invention are practically useful for the treatment of tumour or cancer and exhibit excellent antitumour activities by a simple manner of administration and in a simple formulation for the administration without bringing about side effects. The present invention is based on these discoveries.

Namely, the present invention provides an N-benzoyl-N'-pyrimidinyloxyphenyl urea compound having the formula:

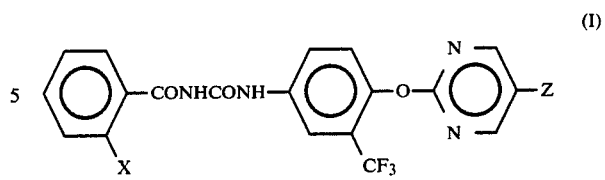

wherein X is a hydrogen atom, a halogen atom, a nitro group or a trifluoromethyl group, and Z is a hydrogen atom or a halogen atom.

The present invention also provides an antitumorous composition containing such a compound as the active ingredient, a method for therapy of cancer by using such a compound, and a process for producing such a compound.

Now, the present invention will be described in detail with reference to the preferred embodiments.

In the above-mentioned formula I, X is preferably a halogen atom or a nitro group. More preferably, X is a nitro group. Likewise, Z is preferably a halogen atom. As the halogen atom for X and Z in the formula I, there may be mentioned a chlorine atom, a bromine atom, an iodine atom, etc.

The N-benzoyl-N'-pyrimidinyloxyphenyl urea compound of the above-mentioned formula I, may be prepared, for instance, as follows:

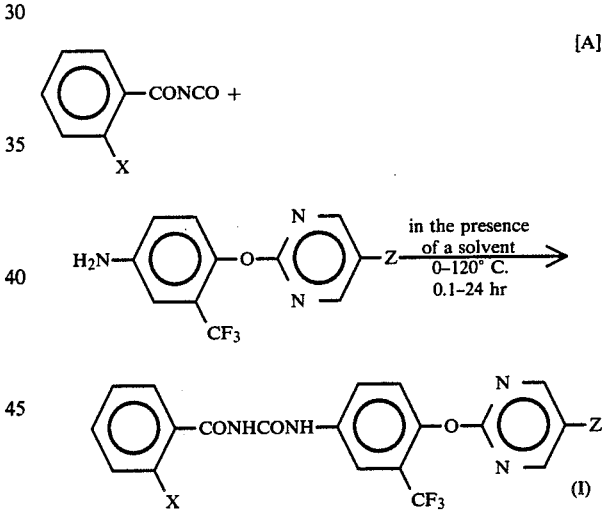

In the above formula, X and Z are as defined above.

As the solvent to be used in the above reaction, there may be mentioned benzene, toluene, xylene, pyridine, dioxane, dimethylsulfoxide, etc.

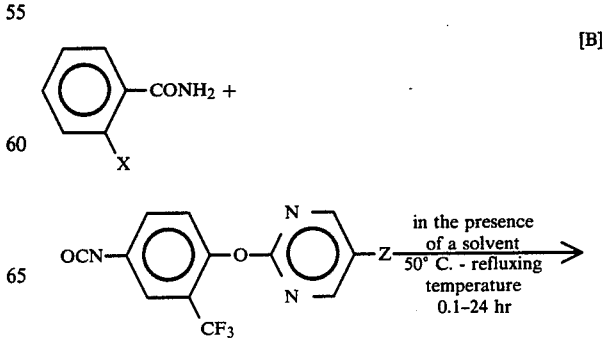

-continued

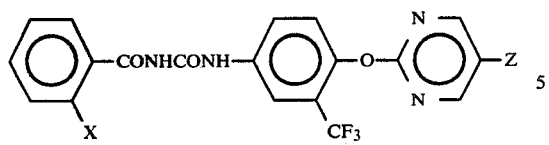

In the formula, X and Z are as defined above.

As the solvent to be used for the above reaction, there may be mentioned toluene, xylene, monochlorobenzene, ethyl acetate, dioxane, etc.

The aniline compound and the phenyl isocyanate compound used as the starting materials in the above reactions may be prepared, for instance as follows:

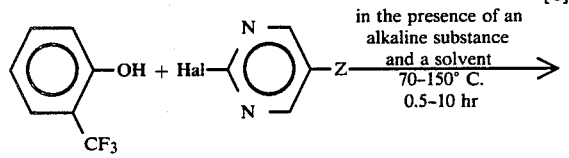
[C]

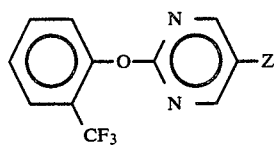

wherein Hal is a halogen atom, and Z is as defined above.

As the alkaline substance to be used, there may be mentioned sodium hydroxide, potassium hydroxide, sodium carbonate, potassium carbonate, etc. As the solvent, there may be mentioned an aprotic polar solvent such as dimethylsulfoxide, dimethylformamide or hexamethylphosphoramide, a ketone such as acetone, methyl ethyl ketone or methyl isobutyl ketone, etc.

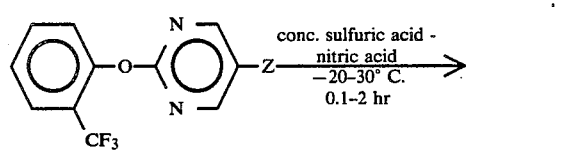

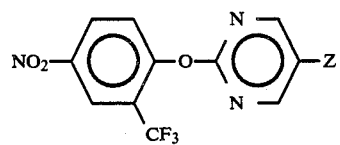

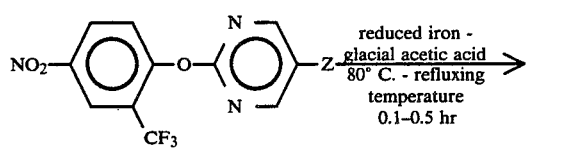

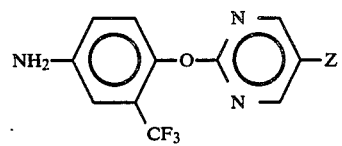

wherein Z is as defined above.

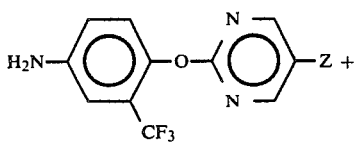
[D]

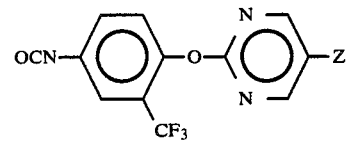

wherein Z is a defined above.

As the solvent to be used, there may be mentioned a solvent inert to phosgene, such as toluene, xylene, monochlorobenzene, ethyl acetate, dioxane, etc.

Now, specific examples for the synthesis of the compounds of the present invention will be described.

SYNTHETIC EXAMPLE 1

Synthesis of N-(N2-nitrobenzoyl)-N'-[4-(5-bromo-2-pyrimidinyloxy)-3-trifluoromethylphenyl]urea (Compound No. 1)

(1) Into a flask, 50 ml of a dimethylsulfoxide solution containing 4.18 g of 5-bromo-2-chloropyrimidine, 3.5 g of 2-trifluoromethylphenol and 5.96 g of potassium carbonate was introduced and stirred at 120° C. for 2 hours. Then, the reaction mixture was poured into water, and extracted with ethyl acetate. The extract was washed with water and dried over anhydrous sodium sulfate. Then, ethyl acetate was distilled off, and the residue was purified by silica gel column chromatography, whereupon 5.03 g of 5-bromo-2-(2-trifluoromethylphenoxy)pyrimidine having a refractive index $(n_D{}^{30.2})$ of 1.5417 was obtained.

(2) Into a flask, 5.0 g of the substituted pyrimidine obtained in the above step (1), was introduced, and dissolved in 25 ml of concentrated sulfuric acid. Then, a solution mixture comprising 1.2 ml of 60% nitric acid and 3 ml of concentrated sulfuric acid, was gradually dropwise added at room temperature over a period of 30 minutes, and the mixture was reacted at room temperature for 20 minutes. After completion of the reaction, the reaction mixture was poured into ice water, and extracted with ethyl acetate. The extract was washed with water, and dried over anhydrous sodium sulfate. Then, ethyl acetate was distilled off to obtain 4.8 g of 5-bromo-2-(2-trifluoromethyl-4-nitrophenoxy)-pyrimidine having a refractive index $(n_D{}^{32.2})$ of 1.5719.

(3) Into a flask, a solution obtained by dissolving 4.8 g of the substituted pyrimidine obtained in the above step (2) in 40 ml of glacial acetic acid, was introduced, and heated to 100° C. Then, 3.69 g of reduced iron was gradually added, and the mixture was refluxed for 5 minutes, and then cooled to room temperature. To the reaction mixture, acetone was added, and the mixture was filtered. Acetone was distilled off under reduced pressure from the filtrate, and ethyl acetate was added to the residue. The mixture was washed with water, then with a sodium hydrogen carbonate solution and further with water, and then dried over anhydrous sodium sulfate. Then, ethyl acetate was distilled off, and the residue was purified by silica gel column chromatography, whereupon 3.42 g of 4-(5-bromo-2-pyrimidinyloxy)-3-trifluoromethylaniline having a melting point of from 140° to 145° C. was obtained.

(4) Into a flask, a solution obtained by dissolving 1.0 g of the substituted aniline obtained in the above step (3) in 10 ml of dioxane, was introduced, and a solution obtained by dissolving 0.89 g of 2-nitrobenzoyl isocyanate in 10 ml of dioxane, was added thereto. The mixture was reacted at room temperature for 5 hours. After completion of the reaction, the product was poured into hot water, and the precipitates were filtered. The crystals thereby obtained were suspended in ethyl acetate, and, after an addition of n-hexane, was filtered, washed with methanol and dried, to obtain 0.82 g of the desired compound having a melting point of from 196° to 197° C.

SYNTHETIC EXAMPLE 2

Synthesis of N-(2-nitrobenzoyl)-N'-[4-(5-chloro2-pyrimidinyloxy)-3-trifluoromethylphenyl]urea (Compound No. 2)

(1) Into a flask, 50 ml of a dimethylsulfoxide solution containing 5.0 g of 2,5-dichloropyrimidine, 6.6 g of 2-trifluoromethylphenol and 9.4 g of potassium carbonate, was introduced, and stirred at 100° C. for 2 hours. Then, the reaction mixture was poured into ice water, and extracted with ethyl acetate. The extract was washed with water, and dried over anhydrous sodium sulfate. Then, ethyl acetate was distilled off, and the residue was purified by silica gel column chromatography, whereupon 7.7 g of 5-chloro-2-(2-trifluoromethylphenoxy)pyrimidine was obtained.

(2) Into a flask, 7.7 g of the substituted pyrimidine obtained in the above step (1) was introduced, and dissolved in 45 ml of concentrated sulfuric acid. Then, a solution mixture comprising 2.1 ml of 60% nitric acid and 10 ml of concentrated sulfuric acid, was gradually dropwise added at room temperature over a period of 30 minutes, and the mixture was stirred at room temperature for 20 minutes. After completion of the reaction, the reaction mixture was poured into ice water, and extracted with ethyl acetate. The extract was washed with water, and dried over anhydrous sodium sulfate. Then, ethyl acetate was distilled off, and the residue was purified by silica gel column chromatography, whereupon 8.4 g of 5-chloro-2-(2-trifluoromethyl-4-nitrophenoxy)pyrimidine was obtained.

(3) Into a flask, a solution obtained by dissolving 8.4 g of the substituted pyrimidine obtained in the above step (2) in 70 ml of glacial acetic acid, was introduced, and heated to 100° C. Then, 7.4 g of reduced iron was gradually added, and refluxed for 10 minutes. Then, the reaction mixture was cooled to room temperature, then poured into water and extracted with methylene chloride. The extract solution was washed with water, and dried over anhydrous sodium sulfate. Then, methylene chloride was distilled off, and the residue was purified by silica gel column chromatography, whereupon 6.0 g of 4-(5-chloro-2-pyrimidinyloxy)-3-trifluoromethylaniline having a melting point of from 154° to 155.5° C. was obtained.

(4) Into a flask, a solution obtained by dissolving 2.0 g of the substituted aniline obtained in the above step (3) in 15 ml of dioxane, was introduced, and a solution obtained by dissolving 1.62 g of 2-nitrobenzoyl isocyanate in 10 ml of dioxane, was added thereto. The mixture was then reacted at room temperature for 16 hours. After completion of the reaction, the product was poured into hot water, and precipitates were filtered. The crystals thereby obtained were suspended in ethyl acetate, and after the addition of n-hexane, subjected to filtration and drying, to obtain 0.8 g of the desired product having a melting point of from 201° to 205° C.

Other compounds of the present invention will be listed as follows:

Compound No. 3:
N-(2-nitrobenzoyl)-N'-[4-(5-iodo-2-pyrimidinyloxy)-3-trifluoromethylphenyl]urea
Melting point: 211°–214° C.
Intermediate of Compound No. 3:
4-(5-iodo-2-pyrimidinyloxy)-3-trifluoromethylaniline
Melting point: 115°–117° C.
Compound No. 4:
N-(2-chlorobenzoyl)-N'-[4-(5-chloro-2-pyrimidinyloxy)-3-trifluoromethylphenyl]urea
Compound No. 5:
N-(2-trifluoromethylbenzoyl)-N'-[4-(5-chloro-2-pyrimidinyloxy)-3-trifluoromethylphenyl]urea
Compound No. 6:
N-(2-bromobenzoyl)-N'-[4-(5-chloro-2-pyrimidinyloxy)-3-trifluoromethylphenyl]urea
Compound No. 7:
N-(2-nitrobenzoyl)-N'-[4-(2-pyrimidinyloxy)-3-trifluoromethylphenyl]urea
Compound No. 8:
N-benzoyl-N'-[4-(5-chloro-2-pyrimidinyloxy)-3-trifluoromethylphenyl]urea Now, the antitumour activities, acute toxicity, doses and administration routes of the N-benzoyl-N'-pyrimidinyloxyphenyl urea compounds of the present invention will be described.

(1) Antitumour activities

TEST EXAMPLE 1

(Intraperitoneal-intraperitoneal)

To BDF$_1$ mice, p-388 leukemia cells were intraperitoneally inoculated in an amount of 1×10$^6$ cells/mouse. A test drug was intraperitoneally administered twice, i.e. one day and four days after the inoculation. The mice were observed for 30 days for survival or death. The ratio (%) of median survival time of test and control animals was obtained with the number of survival days of mice of the control group to which a physiological saline was administered, being evaluated as 100. The results are shown in Table 1. The comparative drugs were dispersions obtained by adding small amounts of surfactants (e.g. Tween-80) to the comparative compounds. The drugs of the present invention were those prepared in accordance with Formulation Example 4 given hereinafter.

TABLE 1

| Compound No. | Dose (Active ingredient mg/kg/day) | T/C (%) of MST[1] |
|---|---|---|
| 1 | 3.125 | 153 |
| 2 | 3.125 | 160 |
| Comparative Compound No. 1 | 25 | 230 |
| | 12.5 | 171 |
| Comparative Compound No. 2 | 200 | 183.9 |
| Comparative Compound No. 3 | 100 | 236.8 |
| Comparative | 100 | 165 |

TABLE 1-continued

| Compound No. | Dose (Active ingredient mg/kg/day) | T/C (%) of MST[1] |
| --- | --- | --- |
| Compound No. 4 | | |

Note: MST[1] Ratio of median survival time of test and control animals

Comparative Compounds Nos. 1 to 4 are disclosed in Japanese Unexamined Patent Publication No. 109721/1982, and their chemical names are as follows:

Comparative Compound No. 1:
N-(2 nitrobenzoyl)-N'-[3-chloro-4-(5-iodo-2-pyrimidinyloxy)phenyl]urea Comparative Compound No. 2:
N-(2-chlorobenzoyl)-N'-[3-chloro-4-(5-chloro-2-pyrimidinyloxy)phenyl]urea Comparative Compound No. 3:
N-(2-chlorobenzoyl)-N'-[3-chloro-4-(5-iodo-2-pyrimidinyloxy)phenyl]urea Comparative Compound No. 4:
N-(2-bromobenzoyl)-N'-[3-chloro-4-(5-iodo-2-pyrimidinyloxy)phenyl]urea

TEST EXAMPLE 2

(intraperitoneal-oral)

To BDF$_1$ mice, p-388 leukemia cells were intraperitoneally inoculated in an amount of $1 \times 10^6$ cells/mouse. A test drug was orally administered twice i.e. one day and four days after the inoculation. The mice were observed for 30 days for survival or death, and the ratio of median survival time of test and control animals was obtained with the number of survival days of mice of the control group to which a physiolocal saline was administered, being evaluated as 100. The results are shown in Table 2. The test drugs and comparative drugs were formulated in accordance with Formulation Example 4 given hereinafter.

TABLE 2

| Compound No. | Dose (Active ingredient mg/kg/day) | T/C (%) of MST[1] |
| --- | --- | --- |
| 1 | 6.25 | 186 |
| 2 | 6.25 | 167 |
| Comparative Compound No. 1 | 1600 | 186 |
| | 800 | 143 |
| | 400 | 116 |

Notes: MST[1] is as defined above.

Comparative Compound No. 1 is the same as mentioned above.

As is evident from the comparative data in Test Example 2, the compounds of the present invention have remarkably high antitumour activities as compared with the comparative compound. The reason is not clearly understood, but it is assumed that due to the differences in the absorption of the drugs by the gut, the drug concentrations in blood and the transfer property of the drugs to the target portions, there may be substantial difference in the arrival of the drugs to the diseased portions, whereby a substantial difference in the antitumour activities is brought about.

(2) Actute toxicity:

To ddY mice (10 animals), a drug containing the Compound No. 1 or No. 2 of the present invention formulated in accordance with Formulation Example 4 was orally administered in an amount of the compound of 12.5 mg/kg, whereupon no mice died. Thus, the acute toxicity values (LD$_{50}$) of the Compounds No. 1 and No. 2 were found to be at least 12.5 mg/kg.

On the other hand, a similar test was conducted by intraperitoneally administering a suspension obtained by adding a small amount of a surfactant (Tween-80) to the Compound No. 3 of the present invention, to the same mice, whereby the LD$_{50}$ values were from 50 to 100 mg/kg.

(3) Doses and administration routes

As to administration routes in the case of animals, the compounds of this invention are administrated as injections such as intraperitoneal injection, intravenous injection, local injection and the like, or as oral drugs. In the case of human beings, said compounds are administrated as injections such as intravascular (intravenous or intraarterial) injection, local injection and the like, or oral drugs, suppositories or the like. As to the dose, said compounds are administrated continuously or intermittently in a range in which the total dose does not exceed a certain level, in consideration of the results of animal experiments and various conditions. However, the dose may, of course, be properly varied depending on the administration route and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists. The antitumorous composition of this invention are prepared in the same manner as for conventional drugs. For example, they are prepared from an active ingredient and various pharmacologically acceptable adjuvants such as inactive diluent and the like. Oral and intravenous administration of these antitumorous compositions is most suitable. The content of the active ingredient in the antitumorous compositions of this invention may vary depending on various conditions and cannot be determined uniquely. It is sufficient that the active ingredient is contained similarly to the case of conventional antitumorous compositions.

The compounds of the present invention are hardly soluble in both water and organic solvents. Therefore, they are preferably formulated into an aqueous suspension which may further contain phospholipids. As a method for producing an aqueous suspension containing no phospholipids, there may be mentioned a method wherein the active compound is preliminarily pulverized into fine powder, then the fine powder of the active compound is added to an aqueous solution containing a surfactant and, if necessary, a defoaming agent, the mixture is pulverized in a wet system until 80% of particles have a particle size of not higher than 5 µm, more preferably not higher than 2 µm, and a thickener is added thereto. As specific examples of the surfactant, there may be mentioned a non-ionic phosphoric acid ester, a polyoxyethylene hardened castor oil, a polyoxyethylene sorbitan fatty acid ester, a sugar ester, a polyoxyethylene polyoxypropylene block polymer, etc. As specific examples of the defoaming agent, there may be mentioned dimethylpolysiloxane, methylphenylsiloxane, a sorbitan fatty acid ester, a polyoxyethylene-polyoxypropylene cetyl ether, silicone, etc. As specific examples of the thickener, there may be mentioned guar gum, alginic acid, gum arabic, pectin, starch, xanthane gum, gelatin, etc. On the other hand, as a method for preparing an aqueous suspension containing a phospholipid, there may be mentioned a method wherein a phospholipid such as soybean phospholipid or yolk phospholipid is used instead of the surfactant in the above-mentioned method, and an antioxidant such as α-tocopherol is used instead of the thickener.

Further, these compounds may be formulated into tablets, capsules, enteric agents, granules, powders, injection solutions or suppositories by common methods for formulations.

Now, Formulation Examples of the antitumour drugs of the present invention will be described.

FORMULATION EXAMPLE 1

70 mg of a non-crystalline powder of the above Compound No. 1 was thoroughly mixed with 30 mg of lactose, and 100 mg of the mixture was filled into a capsule to obtain a capsule drug for oral administration.

FORMULATION EXAMPLE 2

85 parts by weight of a non-crystalline powder of the above Compound No. 3 was uniformly mixed with 1 part by weight of glucose, 10 parts by weight of corn starch and 1.5 parts by weight of a 5% starch paste, and the mixture was granulated by a wet method. Then, 1 part by weight of magnesium stearate was added thereto. The mixture was tableted to obtain tablets for oral administration.

FORMULATION EXAMPLE 3

5 g of the above Compound No. 1 was dissolved in 5 ml of dimethylacetamide, and 25 ml of coconut oil, 7 g of Pegnol HC-17 (manufactured by Toho Kagaku K.K.) and 6 g of HO-10M (manufactured by Toho Kagaku K.K.) were added to obtain an emulsion. To this emulsion, the same amount of sterilized distilled water was added, and the mixture was subjected to ultrasonic treatment for from 20 to 30 seconds to obtain an oily suspension.

FORMULATION EXAMPLE 4

The Compound No. 1 of the present invention was preliminarily pulverized by a centrifugal pulverizer. On the other hand, 5 parts by weight of polyoxyethylene (60) hardened castor oil, 0.2 part by weight of silicone and 0.3 part by weight of a polyoxyethylene-polyoxypropylene block polymer were added to 79.5 parts by weight of a physiological saline to obtain an aqueous solution, to which 10 parts by weight of the above pulverized Compound No. 1 of the present invention was added. The mixture was pulverized in a wet system by a sand mill using glass beads (80% of particles having a particle size of not larger than 2 μm). Then, 5 parts by weight of xanthane gum (2% solution) was added thereto to obtain an aqueous suspension.

FORMULATION EXAMPLE 5

To an aqueous solution obtained by dissolving 1.5 parts by weight of oxyethylated polyallylphenol phosphate and 0.2 part by weight of silicone in 53.3 parts by weight of a physiological saline, 40 parts by weight of the Compound No. 2 of the present invention puverlized by a centrifugal pulverizer, was added, and the mixture was pulverized in a wet system in the sand mill by using glass beads (90% of particles having a particle size of not larger than 2 μm). Then, 5 parts by weight of xanthane gum (2% solution) was added thereto to obtain an aqueous suspension.

FORMULATION EXAMPLE 6

The Compound No. 1 of the present invention was preliminarily pulverized by a centrifugal pulverizer. 5 parts by weight of the pulverized Compound No. 1 of the present invention was added to an aqueous solution obtained by stirring and dispersing 2 parts by weight of yolk phospholipid, 0.001 part by weight of α-tocopherol and 92.999 parts by weight of a physiological saline. Then, the mixture was pulverized in a wet system in a sand mill by using glass beads (80% of particles having particle size of not larger than 2 μm) to obtain an aqueous suspension.

We claim:

1. An N-benzoyl-N'-pyrimidinyloxyphenyl urea compound having the formula:

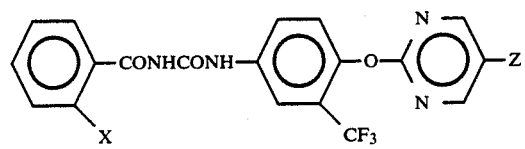

wherein X is a halogen atom, or a nitro group, and Z is a hydrogen atom or a halogen atom.

2. The compound according to claim 1, wherein X is a nitro group and Z is a halogen atom.

3. The compound according to claim 1, which is N-(2-nitrobenzoyl)-N'-[4-(5-bromo-2-pyrimidinyloxy)-3-trifluoromethylphenyl]urea.

4. The compound according to claim 1, which is N-(2-nitrobenzoyl)-N'-[4-(5-chloro-2-pyrimidinyloxy)-3-trifluoromethylphenyl]urea.

5. The compound according to claim 1, which is N-(2-nitrobenzoyl)-N'-[4-(5-iodo-2-pyrimidinyloxy)-3-trifluoromethylphenyl]urea.

6. A composition for treating mammalian leukemia comprising an N-benzoyl-N'-pyrimidinyloxyphenyl urea compound as defined in claim 1 in an amount sufficient to exhibit antileukemia activity and a pharmacologically acceptable adjuvant.

7. A method for treating mammalian leukemia which comprises administering to a mammal an N-benzoyl-N'-pyrimidinyloxyphenyl urea compound as defined in claim 1 in an amount sufficient to exhibit antileukemia activity.

8. An intermediate compound having the formula:

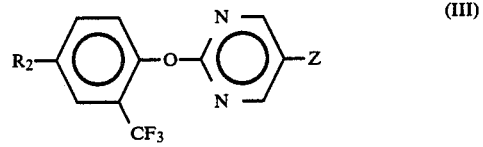

(III)

wherein $R_2$ is an amino group or an isocyanate group, and Z is a hydrogen atom or a halogen atom.

9. The compound according to claim 8, wherein $R_2$ is an amino group, and Z is a hydrogen atom or a halogen atom.

10. The compound according to claim 8, wherein $R_2$ is an amino group, and Z is a halogen atom.

* * * * *